United States Patent [19]

Siegmeier et al.

[11] Patent Number: 4,626,603

[45] Date of Patent: Dec. 2, 1986

[54] PROCESS FOR THE CONTINUOUS PRODUCTION OF VICINAL DIOLS

[75] Inventors: Rainer Siegmeier, Frankfurt; Günter Prescher, Hanau; Helmut Maurer, Rodenbach, all of Fed. Rep. of Germany

[73] Assignee: Degussa Aktiengesellschaft, Frankfurt am Main, Fed. Rep. of Germany

[21] Appl. No.: 798,797

[22] Filed: Nov. 15, 1985

[30] Foreign Application Priority Data

Nov. 24, 1984 [DE] Fed. Rep. of Germany ....... 3442938

[51] Int. Cl.$^4$ ...................... C07C 29/00; C07C 31/20; C07C 35/14

[52] U.S. Cl. .................... 568/833; 568/819; 568/821; 568/823; 568/828; 568/838; 568/857; 568/867

[58] Field of Search ............... 568/867, 833, 819, 821, 568/823, 828, 838, 857

[56] References Cited

U.S. PATENT DOCUMENTS

| | | | |
|---|---|---|---|
| 1,641,710 | 9/1927 | Untiedt | 568/867 |
| 2,236,919 | 4/1941 | Reynhart | 568/867 |
| 2,623,909 | 12/1952 | Robeson et al. | 260/635 |
| 2,784,202 | 3/1957 | Gardner et al. | 568/867 |
| 3,576,890 | 4/1971 | Binning | 260/635 |
| 3,933,923 | 1/1976 | Osberghaus et al. | 568/867 |
| 3,991,126 | 11/1976 | Bacskai | 568/867 |
| 4,087,474 | 5/1978 | Convers et al. | 568/867 |
| 4,107,221 | 8/1978 | Tasto et al. | 568/867 |
| 4,339,616 | 7/1982 | Rutzen et al. | 568/867 |
| 4,390,738 | 6/1983 | Waddan et al. | 568/867 |

FOREIGN PATENT DOCUMENTS 0062234 4/1982 Japan .................. 568/867

OTHER PUBLICATIONS

J. Amer. Chem. Soc., vol. 66 (1944), p. 1925.

Primary Examiner—J. E. Evans
Attorney, Agent, or Firm—Cushman, Darby & Cushman

[57] ABSTRACT

Aliphatic or cyclic epoxides containing 3 to 8 carbon atoms which are present in aromatic hydrocarbons or halohydrocarbons are saponified continuously and directly to vicinal diols without the use of high temperatures and pressures which would otherwise be necessary. The saponification is acid catalyzed.

19 Claims, 1 Drawing Figure

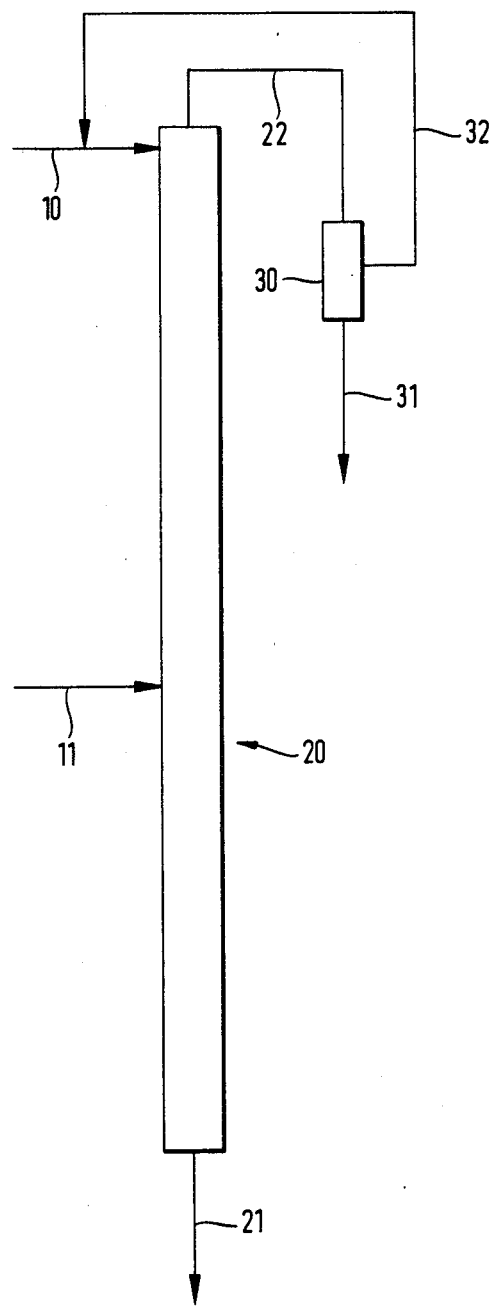

PROCESS FOR THE CONTINUOUS PRODUCTION OF VICINAL DIOLS

BACKGROUND OF THE INVENTION

The invention is directed to the production of vicinal diols, thus diols whose hydroxyl groups are on adjacent carbon atoms, by saponification of the corresponding epoxide.

Vicinal diols hve numerous uses, e.g., as intermediate products in the production of butadiene and isoprene, which are formed from the corresponding diols by dehydration.

Additionally, they play a role as components in the production of polyesters and polyurethanes, as well as in the cosmetic and pharmaceutical industries.

Vicinal diols are produced, among other procedures, by saponification of the corresponding epoxide. Thereby, this saponification is catalyzed both by the addition of acids (see, e.g., the state of the art of U.S. Pat. No. 3,576,890), as well as alkalis (see, e.g., German OS No. 1793247, German OS No. 2203806), as well as salts of aliphatic mono or polycarboxylic acids (German OS No. 2256907), as well as primary, second, or tertiary amine salts or ammonium salts (European published application No. 0025961).

It is also known to produce the acids functioning as catalysts by the addition of esters of lower carboxylic acids and hydrolysis of the esters of alcohols and acids (U.S. Pat. No. 3,576,890).

The saponification can be carried out in pure aqueous medium or in the presence of solvents such as water soluble ketones or cyclic ethers (German OS No. 2256907).

The saponification is carried out not only directly with the epoxides, but it is also possible to form first, e.g., a lower carboxylic acid ester, which then is saponified (J. Amer.Chem.Soc., volume 66, page 1925 (1944). This process is used for the most part with long chain epoxides.

In addition to the yield of diols, the selectivity is also important. The latter is influenced by holding the pH, which is in the weakly acid region, as constant as possible. For this purpose, processes were developed which operate in the presence of carbon dioxide (see U.S. Pat. No. 2,623,909 and German OS No. 2,615,595). Thereby, there must be employed a discontinuous operation in an autoclave under increased pressure, which is in part considerably high, see the examples cited therein.

According to the state of the art in the first line there were saponified either lower epoxides such as ethylene oxide or propylene oxide or higher epoxides having, e.g., 12 to 18 carbon atoms, to the corresponding vicinal diols.

If in this process the general range is given for the number of carbon atoms of the epoxide, which in the lower epoxides goes up to about $C_5$ and in the higher epoxides goes down to about $C_4$, then there is used in the examples ethylene oxide or propylene oxide or higher epoxides with, e.g., 12 to 18 carbon atoms.

The intermediate range of isomeric pentene oxides to heptene oxides in their direct saponification to the corresponding diols, previously has not led to industrial realization.

However, precisely the diols of this intermediate range are essential in the production of, e.g., pesticides.

Therefore, the task of the present invention is the direct saponification of epoxides having 3 to 8, preferably 5 to 7, carbon atoms of the corresponding vicinal diols in good yields and with high selectivity.

SUMMARY OF THE INVENTION

It has now been found that vicinal diols having 3 to 8 carbon atoms can be produced in high yields and selectivity directly and continuously by acid catalyzed saponification with water in the presence of an organic solvent at low pressure and moderate temperatures if a solution of aliphatic linear or branched or cycloaliphatic epoxide having 3 to 8 carbon atoms is saponified with water at 30° to 150° C. at atmospheric pressure or a pressure up to 5 bar in aromatic or halohydrocarbons which are not miscible with water and in the presence of an acid catalyst.

There are included as aliphatic linear or branched or cyclic epoxide having 3 to 8 carbon atoms propylene oxide; 2,3-epoxypropanol-1; 1,2-butene oxide; 2,3-butene oxide; 3,4-epoxybutene-1; 1,2,3,4-butadiene dioxide; 2,3-epoxybutane-diol-1,4; 1,2-epoxy-2-methylbutane; 2-pentene oxide; cyclopentene oxide; 3-methyl-1-butene oxide; 2-methyl-2-butene oxide; 2,3-dimethylbutene oxide-1; 2,3-dimethylbutene oxide-2; 3,3-dimethylbutene oxide-1; 1-hexene oxide; 2-hexene oxide; 3-hexene oxide; cyclohexene oxide; 4-methylpentene oxide-1; 5,6-epoxyhexene-1; 1,2,5,6-diepoxyhexane; 2,3,5,6-diepoxybicyclo-2,2,1-heptane; 2,3-epoxybicyclo-2,2,1-heptane; 1-heptene oxide; 3-heptene oxide; cycloheptene oxide; 1-octene oxide; 7,8-epoxy-octene-1; 1,2,7,8-diepoxyoctane; cyclooctene oxide; 1,2-epoxy-cyclooctene-5; 1,2,5,6-diepoxycyclooctane; 1,2,3,4-diepoxycyclooctane; 1,2-epoxy-cyclooctene-3; 3,4-epoxy-cyclooctanol; 2,3-epoxy-bicyclo-3,3,O-octane; vinylcyclohexene oxide; vinylcyclohexene dioxide.

There have proven as very suitable starting materials pentene oxide-2, hexene oxide-1, neohexene oxide, cyclohexene oxide, heptene oxide-1, thus epoxides having 5 to 7 carbon atoms.

The epoxides, which are produced according to the known processes generally occur in the form of a solution, above all in aromatic or halohydrocarbons (see German AS No. 2519298, German OS No. 2602776). These solutions can be employed directly in the saponification process according to the invention. However, it is also possible to dissolve a commercial epoxide in a solvent and then to saponify this solution according to the invention. For the most part, no additional purification of the commercial product is required.

There may be mentioned as aromatic hydrocarbons, for example, benzene, toluene, o-, m-, p-xylene, ethyl benzene, propyl benzene, pseudocumene, mesitylene. Benzene is especially preferred as the solvent.

Among the halogenated hydrocarbons, there are especially preferred chlorinated hydrocarbons as solvents, e.g., chloroform, propylene dichloride, dichloromethane, and the di and trichlorethanes. Especially suitable is chloroform.

The solvents are employed in such amounts that the epoxide used is dissolved homogeneously. The epoxide is preferably present in solutions which contain 15 to 30 weight percent epoxide, independent of the type of solvent. However, there can also be used both higher and lower concentrated solutions. The weight ratio of epoxide to water is 1:1 to 1:5, preferably at 1:1.5 to 1:2.5.

As acid catalysts, there have proven suitable mineral acids such as sulfuric acid, hydrochloric acid, ortho phosphoric acid, perchloric acid. Sulfuric acid is preferred.

Organic acids which can be used include formic acid, acetic acid, propionic acid, toluenesulfonic acid, isobutyric acid, methanesulfonic acid. Formic acid is preferred.

The catalysts, regardless of whether they are mineral acids or organic acids are used in amounts of 0.05 to 5 weight percent, based on the amount of water.

The preferred saponification temperature is the range of 30° to 120° C. The saponification occurs in customary distillation columns which are preferably operated at atmospheric pressure or at slight superatmospheric pressure up to 5 bar.

The solution of the epoxide is introduced into the middle of the saponification column and the water, which contains the acid catalyst, is added near the top of the column.

In the distillation, the solvent is drawn off at the head of the column, if necessary in the form of an azeotrope with water.

There has proven very favorable a ratio "solvent to water" of 5:1 to 1:1 parts by weight. Very suitable is a ratio of 1.5:1 to 2:1 parts by weight.

The process can comprise, consist essentially of, or consist of the stated steps with the recited materials.

BRIEF DESCRIPTION OF THE DRAWINGS

The single FIGURE of the drawings is a diagrammatic illustration of an apparatus for carrying out the invention wherein an azeotrope with water is drawn off overhead.

DETAILED DESCRIPTION

The solution of epoxide is supplied via line 11 into the middle of the saponification column 20. Fresh water via line 10 mixed with recycle water (via line 32) is added at the top of the column. The water flowing in via line 10 contains the acid catalyst. The azeotrope of solvent and water is drawn off at the head via line 22, the azeotrope is then separated in water separator 30 into water and solvent. The solvent leaves the column via line 31, the water is returned via line 32 into line 10.

An acid aqueous solution of vicinal epoxide in water is obtained in the distillation sump of column 20, which solution is withdrawn via line 21.

The industrial advantage of the process of the invention is in the possibility of carrying out the saponification of the epoxide directly and continuously without the use of high temperature or pressures and thereby obtaining high yields and high selectivity. Furthermore, there are not needed special additives to influence the selectivity. There was not previously known such as simple process for the continuous production of vicinal diols from the corresponding epoxides.

The process is illustrated in more detail in the following examples. In these examples, there are compared the results which were obtained discontinuously with those according to the continuous process of the invention.

The discontinuous experiments were carried out in the presence of solvent (Examples 7 to 12) and without solvent (Examples 1 to 6). The continuous examples according to the invention in the presence of solvent (benzene) carry the numbers 13 to 18.

There were employed propylene oxide, pentene oxide-2, neohexene epoxides, (3,3-dimethyl-1,2-epoxybutane), hexene oxide-1, and cyclohexene oxide as well as octene oxide-1.

The discontinuous experiments 1 to 12 were carried out as follows:

There were present in a three necked flask equipped with a stirrer, internal thermometer, and reflux condenser 100 grams of epoxide. 200 grams of water and in a given case 400 grams of benzene, which mixture was treated with 0.1 weight percent of sulfuric acid and heated to boiling. After the end of the reaction, there were ascertained titrimetically and by gas chromotograph epoxide reaction, yield and the amount of high boiling by-products formed.

For continuous examples 13 to 18, the amounts of epoxides are set forth in Table 1. The benzene solution of the corresponding epoxide was introduced via line 11 in the saponification column 20 according to FIG. 1. Simultaneously, there were fed in via line 10 the amounts of water stated in Table 1 together with the amounts of sulfuric acid stated there. The benzene-water azeotrope passing overhead was separated in the water separator 30 into benzene, which was returned via line 32 into line 10, and into water.

The vicinal diol was drawn off in aqueous acid solution via line 21. The results of the discontinuous examples with and without solvent, as well as the continuous examples of the invention are set forth in Table 2.

There was ascertained as the saponification time for the continuous examples 1.4 to 1.6 hours, depending on the throughput.

From Table 2, it is clear that there is an increase in yield according to the continuous method in the presence of a solvent as well as substantial increase in the selectivity (amount of high boiling by-products) compared to the discontinuous process. While the presence of the solvent in the discontinuous process brought about a certain improvement in the selectivity, there was no general improvement of the yield (Examples 7 to 12 compared to Examples 1 to 6), in the process of the invention there were improved considerably both yield and selectivity.

The entire disclosure of German priority application No. P3442938.7 is hereby incorporated by reference.

TABLE 1

| Epoxide | Input/h g | Amount of Water/h g | Conc. H$_2$SO$_4$ Wt. % | Product |
|---|---|---|---|---|
| Propylene oxide | 102 | 212 | 1 | Propanediol-1,2 |
| Pentene oxide-2 | 95 | 185 | 0.1 | Pentanediol-2,3 |
| Hexene oxide-1 | 107 | 212 | 0.1 | Hexanediol-1,2 |
| Neohexene oxide-1 | 106 | 210 | 1 | Neohexanediol-1,2 |
| Cyclohexene oxide | 111 | 216 | 0.1 | Cyclohexanediol-1,2 |
| Octene oxide-1 | 106 | 212 | 0.3 | Octanediol-1,2 |

The epoxide was employed in each case as an about 20 wt. % solution in benzene.

TABLE 2

| No. | Epoxide | Solvent | Conc. H₂SO₄ Wt. % | Reaction Time h | Yield % | High Boiling By-Product g/100 g Diol |
|---|---|---|---|---|---|---|
| | | Discontinuous, Without Solvent | | | | |
| 1 | Propylene oxide | — | 0.1 | 0.6 | 77 | 18.2 |
| 2 | Pentene oxide-2 | — | 0.1 | 0.3 | 87 | 7.4 |
| 3 | Hexene oxide-1 | — | 0.1 | 0.3 | 88 | 10.5 |
| 4 | Cyclohexene oxide | — | 0.1 | 0.2 | 94 | 3.5 |
| 5 | Neohexene oxide-1 | — | 1.0 | 0.3 | 86 | 10.4 |
| 6 | Octene oxide-1 | — | 0.1 | 1.5 | 76 | 19.6 |
| | | Discontinuous, With Solvent | | | | |
| 7 | Propylene oxide | Benzene | 0.1 | 1.2 | 77 | 15.6 |
| 8 | Pentene oxide-2 | " | 0.1 | 8 | 87 | 6.0 |
| 9 | Hexene oxide-1 | " | 0.4 | 7 | 84 | 11.2 |
| 10 | Cyclohexene oxide | " | 0.1 | 0.5 | 96 | 1.2 |
| 11 | Neohexene oxide-1 | " | 3.0 | 4.2 | 79 | 14.2 |
| 12 | Octene oxide-1 | " | 3.0 | 4 | 64 | 26.0 |
| | | According to the Invention, Continuous Process | | | | |
| 13 | Propylene oxide | Benzene | 1.0 | — | 95 | 4.2 |
| 14 | Pentene oxide-2 | " | 0.1 | — | 99 | 0.8 |
| 15 | Hexene oxide-1 | " | 0.1 | — | 99 | 0.8 |
| 16 | Cyclohexene oxide | " | 0.1 | — | 99 | 0.3 |
| 17 | Neohexene oxide-1 | " | 1.0 | — | 99 | 0.2 |
| 18 | Octene oxide-1 | " | 0.3 | — | 89 | 8.1 |

What is claimed is:

1. A continuous process for the production of a low molecular weight vicinal diol by acid catalyzed saponification in a column in the presence of an organic solvent at low pressure and moderate temperature comprising continuously (1) supplying a solution of an aliphatic or cycloaliphatic epoxide having 3 to 8 carbon atoms in an aromatic hydrocarbon or a halohydrocarbon solvent which is not miscible with water to the middle of the column, (2) adding a mixture of fresh water and recycled water containing acid catalyst at the top of the column, saponifying the epoxide in the column at 30° to 150° C. at atmospheric pressure or a pressure up to 5 bar, (3) drawing off an azeotrope of solvent and water at the head of the column, (4) separating the azeotrope into (a) water and (b) solvent, (5) removing the solvent from the system, (6) returning the water to the top of the column and (7) drawing off an acid aqueous solution of vicinal diol from the sump of the column.

2. A process according to claim 1 wherein the epoxide has 5 to 7 carbon atoms.

3. A process according to claim 1 wherein there is used benzene or chloroform as the solvent.

4. A process according to claim 3 wherein the solvent is benzene.

5. A process according to claim 3 wherein the epoxide employed in hexene oxide-1, neohexene oxide-1, or cyclohexene oxide.

6. A process according to claim 5 wherein the solvent is benzene.

7. A process according to claim 1 wherein the epoxide employed is hexene oxide-1, neohexene oxide-1, or cyclohexene oxide.

8. A process according to claim 5 wherein the epoxide and water are employed in the weight ratio of 1:1 to 1:5.

9. A process according to claim 8 wherein the epoxide and water are employed in the weight ratio of 1:1.5 to 1:2.5.

10. A process according to claim 1 wherein the epoxide and water are employed in the weight ratio of 1:1.5 to 1:2.5.

11. A process according to claim 8 wherein there is employed a ratio of solvent to water of 5:1 to 1:1 parts by weight.

12. A process according to claim 1 wherein there is employed a ratio of solvent to water of 5:1 to 1:1 parts by weight.

13. A process according to claim 9 wherein there is employed a ratio of solvent to water of 1.5:1 to 2:1 parts by weight.

14. A process according to claim 13 wherein the acid catalyst is employed in an amount of 0.05 to 5 weight percent based on the amount of water.

15. A process according to claim 1 wherein the acid catalyst is employed in an amount of 0.05 to 5 weight percent based on the amount of water.

16. A process according to claim 1 wherein there is employed as the catalyst a mineral acid.

17. A process according to claim 16 wherein the mineral acid is sulfuric acid, hydrochloric acid, ortho phosphoric acid, or perchloric acid.

18. A process according to claim 1 wherein there is employed as the catalyst an organic acid.

19. A process according to claim 18 wherein the catalyst is formic acid, acetic acid, propionic acid, toluenesulfonic acid, methanesulfonic acid, or isobutyric acid.

* * * * *